(12) United States Patent
Hoopai (10) Patent No.: US 9,724,717 B2
(45) Date of Patent: Aug. 8, 2017

(54) ADJUSTABLE SUPPORT FOR TUBULAR MEDICAL DEVICE PROCESSING

(71) Applicant: Abbott Cardiovascular Systems Inc., Santa Clara, CA (US)

(72) Inventor: Adam K. Hoopai, Poway, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 0 days.

(21) Appl. No.: 14/949,377

(22) Filed: Nov. 23, 2015

(65) Prior Publication Data

US 2016/0144389 A1     May 26, 2016

Related U.S. Application Data (62) Division of application No. 13/273,133, filed on Oct. 13, 2011, now Pat. No. 9,199,261.

(51) Int. Cl.
| | |
|---|---|
| *B05B 13/02* | (2006.01) |
| *B05D 1/00* | (2006.01) |
| *B29C 33/56* | (2006.01) |
| *A61F 2/82* | (2013.01) |

(52) U.S. Cl.
CPC ............ *B05B 13/0207* (2013.01); *A61F 2/82* (2013.01); *B05B 13/0228* (2013.01); *A61F 2230/0069* (2013.01); *A61F 2240/00* (2013.01); *A61F 2240/001* (2013.01); *A61F 2250/001* (2013.01); *A61F 2250/0007* (2013.01); *B05D 1/002* (2013.01); *B22F 2302/00* (2013.01); *B29C 33/56* (2013.01); *Y10T 29/49815* (2015.01); *Y10T 29/49822* (2015.01); *Y10T 29/49824* (2015.01); *Y10T 29/49826* (2015.01); *Y10T 29/49881* (2015.01)

(58) Field of Classification Search
CPC . B05B 13/0207; B05B 13/0228; B05D 1/002; B22F 2302/00; B29C 33/56; A61F 2/82; A61F 2240/00; A61F 2240/001; A61F 2250/001; A61F 2250/007; Y10T 29/49881; Y10T 29/49815; Y10T 29/49822; Y10T 29/49824; Y10T 29/49826
USPC ............. 29/527.1, 527.2, 426.1, 426.5, 559; 427/2.1, 2.24, 2.25; 118/500; 623/1.11
See application file for complete search history.

(56) References Cited

U.S. PATENT DOCUMENTS

| | | | | |
|---|---|---|---|---|
| 4,733,665 | A | * | 3/1988 | Palmaz ..................... A61F 2/91 604/104 |
| 4,800,882 | A | * | 1/1989 | Gianturco ............... A61F 2/885 606/194 |

(Continued)

OTHER PUBLICATIONS

International Search Report for PCT/US2012/050798, mailed Nov. 22, 2012, 5 pgs.

*Primary Examiner* — Christopher Besler
*Assistant Examiner* — Bayan Salone
(74) *Attorney, Agent, or Firm* — Squire Patton Boggs (US) LLP (57) ABSTRACT

An apparatus and method for supporting a tubular medical device, such as a stent or scaffold, includes a rod disposed between two collets. The rod can be shaped to form a range of different size or length helical supports to support a wide range of tubular medical devices. The rod is shaped into a full or partial helix by rotating one of the collets relative to the other.

21 Claims, 7 Drawing Sheets

(56) References Cited

U.S. PATENT DOCUMENTS

| | | | | |
|---|---|---|---|---|
| 4,886,062 A * | 12/1989 | Wiktor | ............... | A61F 2/88 267/180 |
| 5,507,768 A * | 4/1996 | Lau | ............... | A61F 2/958 604/103.05 |
| 5,514,154 A * | 5/1996 | Lau | ............... | A61F 2/88 606/108 |
| 5,569,295 A * | 10/1996 | Lam | ............... | A61F 2/91 606/195 |
| 6,818,063 B1 * | 11/2004 | Kerrigan | ............... | B05C 13/025 118/500 |
| 6,972,054 B2 * | 12/2005 | Kerrigan | ............... | B05C 13/025 118/500 |
| 7,232,490 B1 * | 6/2007 | Hossainy | ............... | B05B 13/0235 118/320 |
| 7,306,677 B2 | 12/2007 | Robida | | |
| 7,335,265 B1 * | 2/2008 | Hossainy | ............... | B05D 1/002 118/307 |
| 7,335,391 B1 | 2/2008 | Pacetti | | |
| 7,354,480 B1 | 4/2008 | Kokish et al. | | |
| 7,402,329 B2 * | 7/2008 | Pacetti | ............... | A61F 2/91 427/2.1 |
| 7,485,333 B2 * | 2/2009 | Pacetti | ............... | B05B 13/0442 118/500 |
| 7,794,777 B2 * | 9/2010 | Kokish | ............... | B05B 13/0228 118/500 |
| 8,003,156 B2 * | 8/2011 | Van Sciver | ............... | B05D 1/02 118/230 |
| 8,069,814 B2 * | 12/2011 | Guerriero | ............... | B05D 1/02 118/500 |
| 8,092,864 B2 * | 1/2012 | Isch | ............... | A61F 2/88 427/2.24 |
| 8,397,666 B2 * | 3/2013 | Delap | ............... | B05B 13/0228 118/320 |
| 8,453,598 B2 * | 6/2013 | Plans | ............... | A61F 2/82 118/500 |
| 8,465,789 B2 * | 6/2013 | Van Sciver | ............... | B05D 1/02 118/319 |
| 8,573,148 B2 * | 11/2013 | Pacetti | ............... | B05B 13/0442 118/500 |
| 8,596,215 B2 * | 12/2013 | Van Sciver | ............... | B05D 1/02 118/500 |
| 8,637,110 B2 * | 1/2014 | Van Sciver | ............... | B05D 1/02 118/500 |
| 8,689,728 B2 * | 4/2014 | Adolfo | ............... | B05B 13/0442 118/500 |
| 8,741,379 B2 * | 6/2014 | Van Sciver | ............... | B05D 1/02 118/230 |
| 9,199,261 B2 * | 12/2015 | Hoopai | ............... | B05B 13/0207 |
| 2004/0062853 A1 * | 4/2004 | Pacetti | ............... | A61F 2/91 427/2.1 |
| 2005/0069630 A1 * | 3/2005 | Fox | ............... | A61F 2/07 427/2.24 |
| 2005/0166841 A1 * | 8/2005 | Robida | ............... | B05B 13/0207 118/500 |
| 2006/0284383 A1 * | 12/2006 | Brettell | ............... | B23B 31/404 279/2.1 |
| 2007/0259100 A1 * | 11/2007 | Guerriero | ............... | B05D 1/02 427/2.24 |
| 2008/0067728 A1 * | 3/2008 | Plans | ............... | A61F 2/82 269/47 |
| 2008/0124452 A1 * | 5/2008 | kokish | ............... | B05B 13/0228 427/2.25 |
| 2008/0280025 A1 * | 11/2008 | Scheer | ............... | A61F 2/91 427/2.24 |
| 2011/0059227 A1 * | 3/2011 | Pacetti | ............... | B05B 13/0442 427/2.25 |
| 2013/0071549 A1 | 3/2013 | Chen et al. | | |
| 2013/0091680 A1 * | 4/2013 | Hoopai | ............... | B05B 13/0207 29/428 |

* cited by examiner

ADJUSTABLE SUPPORT FOR TUBULAR MEDICAL DEVICE PROCESSING

BACKGROUND OF THE INVENTION

Field of the Invention

The present invention relates to drug-eluting medical devices; more particularly, this invention relates to support structure for medical devices. The support structure is used to support the medical device during processing of the medical device, in particular, when a coating is applied to the medical device.

Background of the Invention

Stents are often modified to provide drug delivery capabilities to further address thrombosis and restenosis. Stents may be coated with a polymeric carrier impregnated with a drug or therapeutic substance. A conventional method of coating includes applying a composition including a solvent, a polymer dissolved in the solvent, and a therapeutic substance dispersed in the blend and applied to the stent by immersing the stent in the composition or by spraying the composition onto the stent. The solvent is allowed to evaporate, leaving on the stent strut surfaces a coating of the polymer and the therapeutic substance impregnated in the polymer. Depending on the application and volatility of the solvent, forced air drying may also be used to remove the solvent from the coating and arrive at a desired release rate for the impregnated therapeutic agent into the body.

It is known that some methods for coating stents do not produce an ideal, or defect-free coating over a surface of the stent where the therapeutic agent is intended to take effect. Coating defects may include non-uniform surface characteristics, such as bare spots and flaking. Coating defects can also serve as an initiation site for later-developed peeling or flaking that produces embolic debris. Rough surfaces generated by, and stagnant regions of blood flow produced by nearby flaps or packets formed by coating defects can serve as a nidus for thrombus formation. Furthermore, coating defects produce variations in the intended amount, concentration, and release rate of the drug from the stent coating, further complicating or minimizing the effectiveness of therapeutic agents.

Methods for spray coating a stent with polymer-drug dissolved in a solvent include mounting the stent on a mandrel to support and rotate the stent while it is being sprayed with the drug-polymer composition. Examples of prior mandrel designs constructed for this purpose are disclosed in U.S. Pub. No. 2007/0259100.

A support mandrel is used to hold and keep track of stents during processing. Since stents of a particular type will have different lengths or diameters, several different mandrels are needed to accommodate different stent sizes. Additionally, differently sized mandrels are needed to support different diameter stents as they are being tested or evaluated. It is desirable to have a mandrel that could be adjusted to support stents of different sizes. Many of the stent-supporting mandrels previously proposed can be adjusted to support stents of different lengths. What is needed, however, is a mandrel that can be readily adjusted to support stents of different diameters and lengths, or to adjust the amount of support needed for a stent during testing so that a single mandrel can be used to support a wider variety of stents.

In view of the foregoing, there is a need for a mandrel assembly that provides minimal contact to reduce coating defects during spraying while being adjustable to offer a variable amount of support for stents having a range of different diameters as well as lengths.

SUMMARY OF THE INVENTION

The invention improves on the art by providing an apparatus and method for applying a coating composition to a surface of a tubular medical device, e.g., a stent or scaffold, using an assembly including a rod that can be adjusted for different stent diameters, stent lengths, and/or to vary the amount of support for a stent without requiring an assortment of separate pieces for the mandrel.

In one aspect there is an assembly for supporting a stent during processing, e.g., inspection of the stent, spraying, weighing or drying to remove a solvent from the stent. The assembly includes a first rod extending between first and second members, e.g., first and second collets of a mandrel. A second rod also extends between the two members. This rod can be shaped to provide a support for stents having different diameters by rotating one of the members relative to the other member. When the desired diameter is found, the two members may be locked in rotation, or are capable of retaining their angular positions without the need to provide a locking mechanism, to provide the desired shape for supporting the stent. The shape may be a helix, a partial helix, or the rod may be shaped so that it at least partially circumscribes a longitudinal axis of the first rod. A partial helix means a shape following the path of a helix but traversing less than one full revolution, i.e., circumscribes less than one full circumference of a circle. A rod shaped into a partial helix means a rod that traverses more than about 90 degrees, or between about 90 and 180 degrees, or between about 180 and 270 degrees, or between 270 degrees and less than 360 degrees.

According to another aspect of the invention, a support assembly for a tubular medical device includes first and second collets and a first and second rod extending there between. The second collet includes a collar and a housing adapted for being rotated about the collar. The first rod passes through the collar and the second rod passes through the housing. A gear mechanism is formed between the collar and housing. When the housing is clocked about the collar in fixed angular increments, the second rod may be shaped into different helix shapes. There may be a third rod that also passes through the housing. In this embodiment rotation of the housing forms parallel helix forms for supporting the medical device.

According to one embodiment, an apparatus includes first and second collets and a first and second rod extending between and connected to the collets. The first rod has a longitudinal axis. And the second collet includes a collar receiving the first rod, and a housing receiving the second rod, mounted upon the collar and adapted for being rotated about the collar, wherein the first rod is capable of being formed into a full or partial helix for supporting a medical device between the collets when the housing rotates about the collar.

According to another embodiment, a method of making a support for a tubular medical device includes the steps of disposing the medical device on a rod extending between first and second members and while the medical device is disposed on the rod, rotating the second member relative to the first member to form the second rod as a full or partial helix for supporting the medical device. The second member may include a gear mechanism, or collar and sleeve to provide a clocked rotation about a rotation axis, or it may have only a central passage for the first rod. The second member is rotated about the first rod to shape the second rod. After the desired shape has been made, the second member is fixed to the first rod. Alternatively, the first rod may be fixed to the second member and the first member free to rotate about the first rod to shape the second rod into a full or partial helix. After the desired shape is made, the first member is fixed to the first rod.

According to another embodiment, a method for supporting a medical device includes disposing the medical device between a first and second member, wherein a first and second rod extend through the bore of the stent. The first and second rods are coupled to the first and second members. The first member is held in one hand and the second member is held in the other hand. The second member is rotated relative to the first member to shape the first rod as a support for the stent. After the first rod is shaped, the first and second members are fixed in rotation to the second rod to maintain the shape in the first rod.

According to another embodiment, a method for supporting a second medical device (MD) includes the steps of providing a first MD on a mandrel, the mandrel having a first collet, second collet and a rod extending there between, the rod providing a support for the first MD at about the same diameter as an inner diameter of the first MD; removing the first MD from the rod; placing the second MD on the rod; and shaping the rod to provide a support for the second MD at about the same diameter as an inner diameter of the second MD including rotating the second collet relative to the first collet.

According to another embodiment, a method of applying a coating composition to a medical device includes the steps of providing a medical device on a rod extending between a first and second member; while the medical device rests on the rod, forming the rod into a helix or partial helix by rotating the second member relative to the first member, the helix or partial helix supporting the medical device; locking the second member in rotation relative to the first member to maintain the rod as a helix or partial helix; rotating the medical device about an axis; and applying the coating composition to the rotating medical device.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

DETAILED DESCRIPTION OF EMBODIMENTS

When spraying stents with a drug/polymer mixture it is critical to minimize the defects in the coating caused by the contact of the stent to the spraying mandrel on which it sits while being sprayed. When a drug eluting stent (DES) is implanted, coating defects can cause adverse reactions in the body. In addition, defective coatings can break off and form emboli, or protruding coating can be an initiation point for thrombus formation. Uncoated areas will not contain the intended drug, which can lead to restenosis.

A stent typically has a plurality of undulating, e.g., sinusoidal, ring structures that collectively provide a radial stiffness for the stent, and struts connecting the cylindrical elements. Lengthwise the stent is supported typically by only the flexural rigidity of slender-beam-like linking or connecting elements, which structure may give the stent a desired longitudinal flexibility. Examples of structure and surface topology of a stent are disclosed by U.S. Pat. Nos. 4,733,665, 4,800,882, 4,886,062, 5,514,154, 5,569,295, and 5,507,768. Additionally, this disclosure adopts the stent structure terminology of FIGS. 1-3, paragraphs [026] through [035], et seq. of U.S. application Ser. No. 12/554,671. The following description will refer to a stent supported on an assembly according to the disclosure, but it is understood that the assembly may be used to support a variety of tubular medical devices, including bioresorbable scaffolds.

Figure 1A:
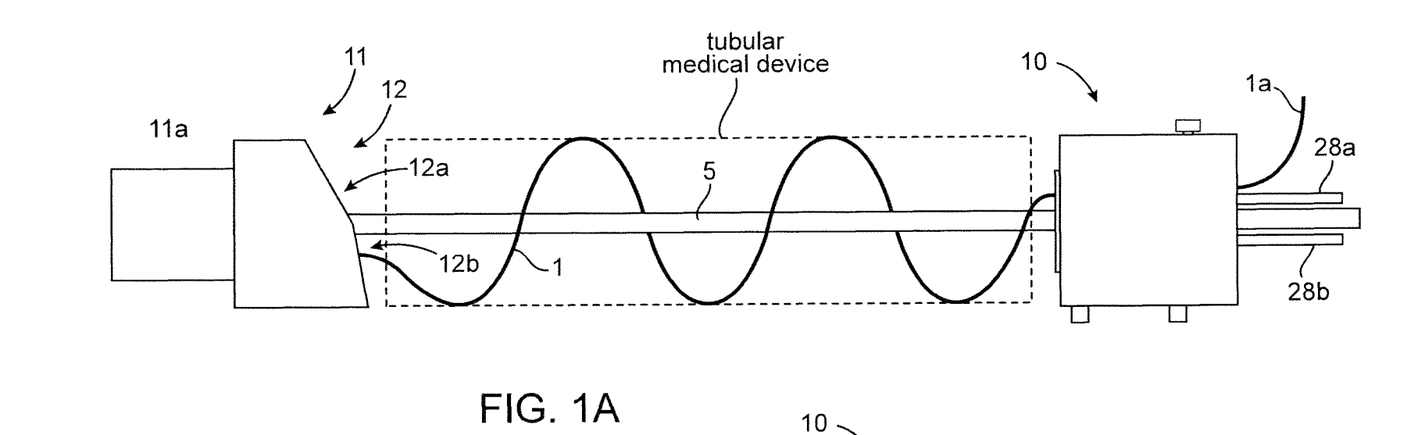
FIG. 1A is a side view of an assembly for supporting a tubular medical device according to the disclosure.
Figure 1B:
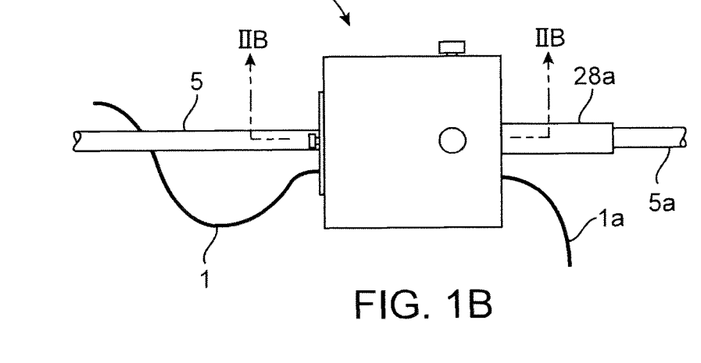
FIG. 1B is a top view of a portion of the assembly of FIG. 1A showing a collet used to form a rod of FIG. 1A into a shape for supporting medical devices of different diameters.

Referring to FIGS. 1A and 1B, there is shown a side and partial top view, respectively, of an assembly for supporting a stent according to the disclosure. FIG. 1A shows the general dimensions (in phantom) of a tubular medical device, e.g., a stent, that can be supported on a helix-shaped supporting rod 1 according to the disclosure. Located at a proximal end of the assembly is a collet 11. Located at a distal end of the assembly is a collet 10. The rod 1 is attached to each of these collets. The collets 10, 11 are fixed in position when maintaining the rod 1 helix shape. The collets 10, 11 also provide abutting surfaces to maintain the stent's position between the collets 10, 11 during processing or handling. Optionally, the collets 10, 11 can also provide supporting surfaces for the stent's ends.

Figure 1C:
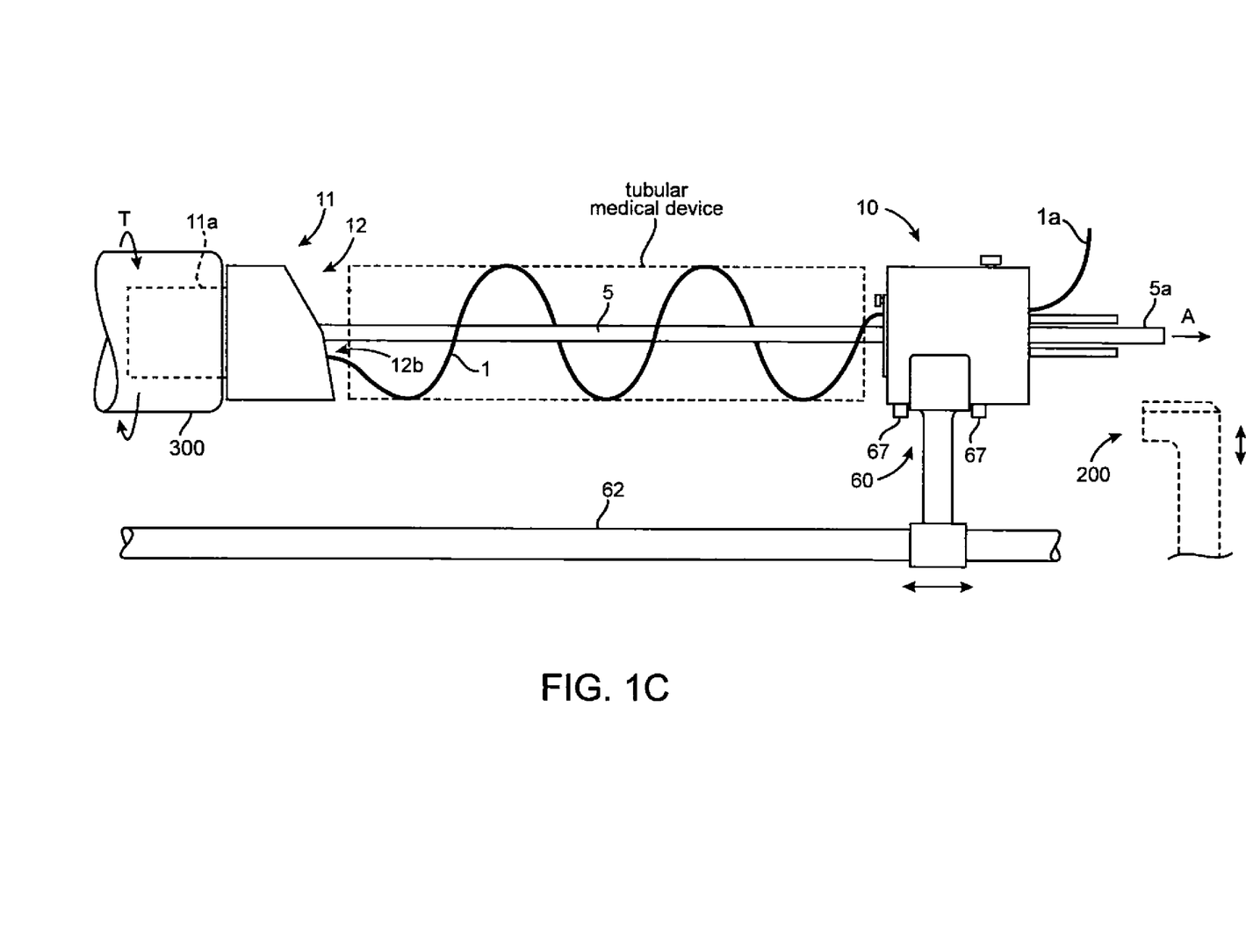
FIG. 1C is a side view of the assembly of FIG. 1A mounted to a spindle of a stent spraying and drying apparatus.

A second rod 5 extends along the rotation axis A (see FIG. 1C). The rod 5 is received in openings provided in each collet 10, 11 for holding the rod 5. As shown the collets 10, 11 are spaced appropriately for the stent length and the diameter of the rod 1 helix chosen to provided a loose supporting surface along the luminal surface of the stent. In this configuration the rod 1 is formed into about a two and one-half revolution helix between the collets 10, 11. As explained in greater detail, below, the rod 1 may be adjusted to form more or less revolutions of a helix, or the diameter of the helix may be increased/decreased as desired to support the stent. This adjustment is done using the collet 10.

A stent may be transported among processing, weighing or inspection stations using the assembly of FIG. 1A. FIG. 1C shows the assembly of FIG. 1A coupled to a spindle 200 with collet 10 supported on a cup or half-collar 60 that slides along a rail 62 (a rim 67 may be formed on collet so that half-collar 60 can move the assembly left or right in FIG. 1C). When applying a spray coating to the stent, an electric motor delivers a torque (T) through the spindle 200 to collet 11, and thus the entire assembly shown in FIG. 1A. An attachment portion 11a of collet 11 includes suitable slots or other structure (not shown) for connecting the collet 11 via attachment portion 11a in rotation about axis A to the spindle 200. The rod 5 connection between each collet 10, 11 can be relied on to deliver the torque T from collet 11 to collet 10 and resist unwinding of the helix as it can be rotationally fixed to both collets.

A stent may be moved between a spraying and drying station one or more times to deliver several layers of a drug-polymer coating to the stent. In FIG. 1C the movement of the stent to/from a spraying or drying station is via displacement along axis A. The stent and assembly may be supported on the distal end for this movement, and/or during a spraying and drying, or drying-only cycle, using half-collar 60 that translates with the assembly and motor spindle 200 over the rail 62. Alternatively, half-collar 60 is not used. Instead, gripper arms 200 are used to engage and support the distal end 5a of rod 5. As indicated, gripper arms 200 extend up and down to grab the end 5a when the assembly is positioned over or under, respectively, the dryer or spray nozzle. Examples of grippers for a drying or spraying process are described in U.S. application Ser. No. 13/235,238. Alternatively, the assembly may be supported as a cantilever from the motor spindle 200. The assembly is configured for rotation about axis A, which is collinear with longitudinal axis of rod 5.

Referring again to FIG. 1A, the collet 11 may have a face 12 forming two slanted surfaces, as shown, for abutment with, or to support an end of the stent, as mentioned earlier. The stent-abutting face 12 of collet 11 may take a variety shapes that have been proposed previously for collets, e.g., flat, grooved or cone-shaped. The collet 11 has a passage or hole 12a for holding one end of the rod 5 and a second hole or passage 12b for holding one end of the rod 1. The rod 1 may be secured in hole 12b so that it cannot rotate about within the hole 12b, to facilitate forming a helix shape. Similarly, the rod 5 may be tightly held in the hole 12a so that there is no relative rotation between it and collet 11 when a torque is applied to collet 11.

Figure 2A:
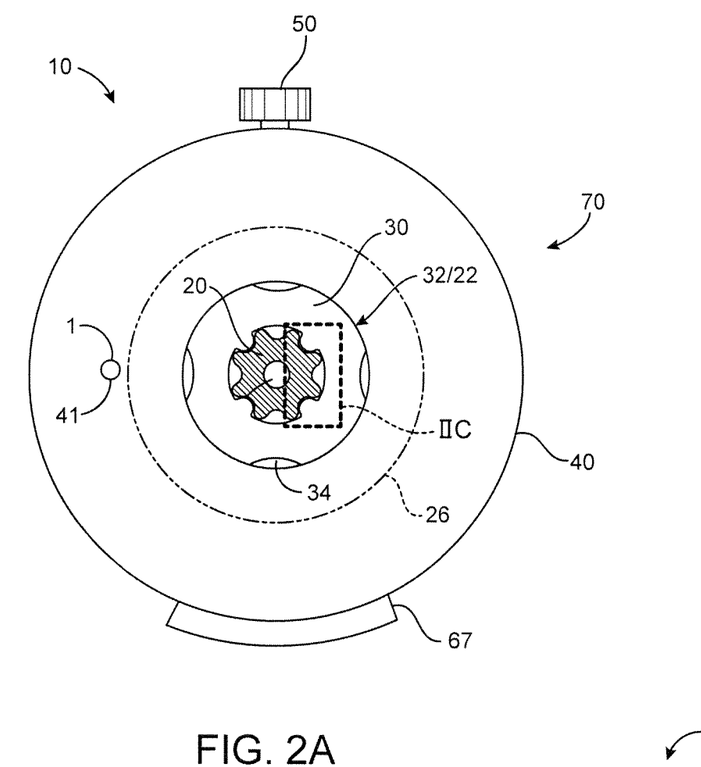
FIG. 2A is a front view of the collet of FIG. 1B as viewed from section IIA-IIA in FIG. 2B.
Figure 2B:
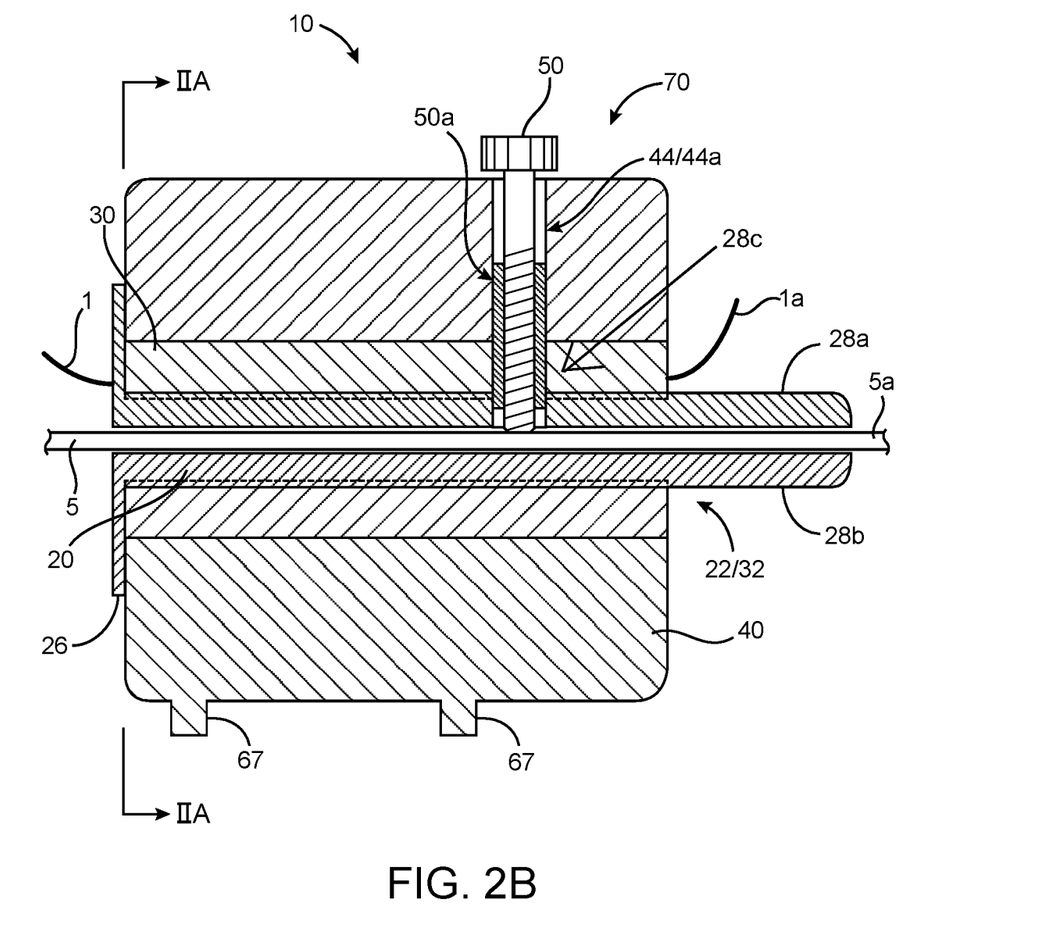
FIG. 2B is a side cross-sectional view of the collet of FIG. 1B, as viewed from section IIB-IIB in FIG. 1B.
Figure 2C:
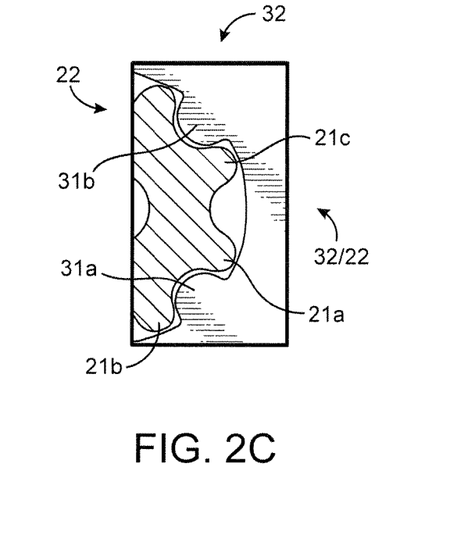
FIG. 2C is a close-up of a portion of the collet of FIG. 2A showing an engagement between teeth formed on a sleeve and collar portion of the collet.

Referring to FIGS. 2A-2C, the collet 10 is adjustable, both lengthwise and rotationally relative to collet 11 of the assembly of FIG. 1A. FIGS. 2A and 2B show a cross-sectional front view and side view, respectively of the collet 10 from FIGS. 1A and 1B. FIG. 2A is taken from the view IIA-IIA as shown in FIG. 2B. FIG. 2B is taken from view IIB-IIB as shown in FIG. 1B. A collar 20 and sleeve 30 component parts of the collet 10 according to one embodiment are shown in the perspective views of FIGS. 3-4.

Collet 10 has holes or passages for receiving ends, respectively, of rods 1 and 5. For collet 10 these holes or passages extend through the collet 10 body to provide for length adjustment for rod 1, or to position collet 10 closer or further from collet 11 to accommodate different length stents. As indicated the ends 5a and 1a of rods 5 and 1, respectively, extend through the body of collet 10 and exit to the right of the collet body as indicated in the figures. The collet 10 includes collar 20 which forms a passage or hole 24 for rod 5. The rod 5 slides within passage 24 to adjust the distance between collets 10 and 11. The collar 20 has a circular flange 26 at the end facing collet 11 and a pair of deflectable leafs 28a, 28b at the opposite end for gripping the collar 20 when the collet 10 is rotationally positioned to form the helix, as explained in greater detail below.

Figure 3:
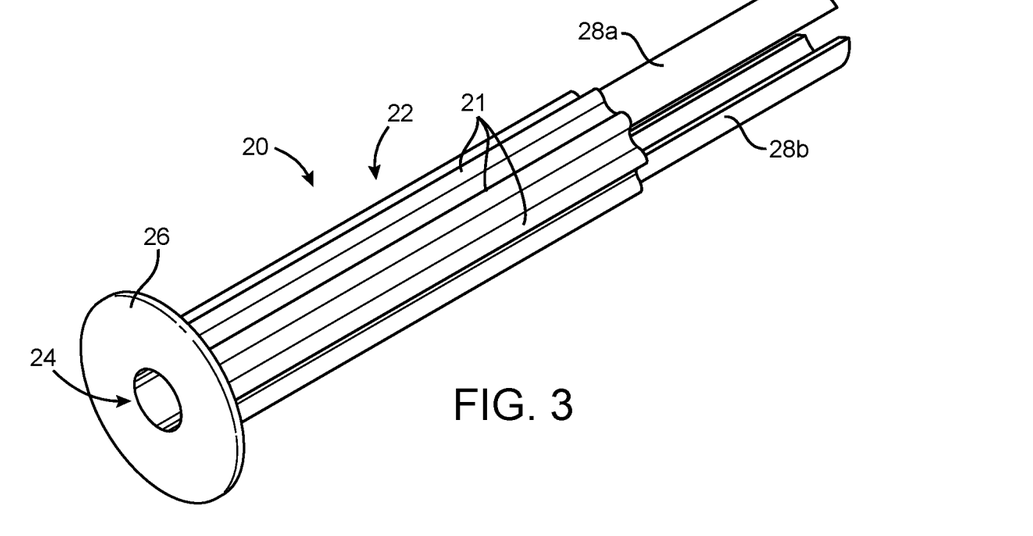
FIG. 3 is a perspective view of the collar of the collet illustrated in FIGS. 1A-1C.
Figure 4:
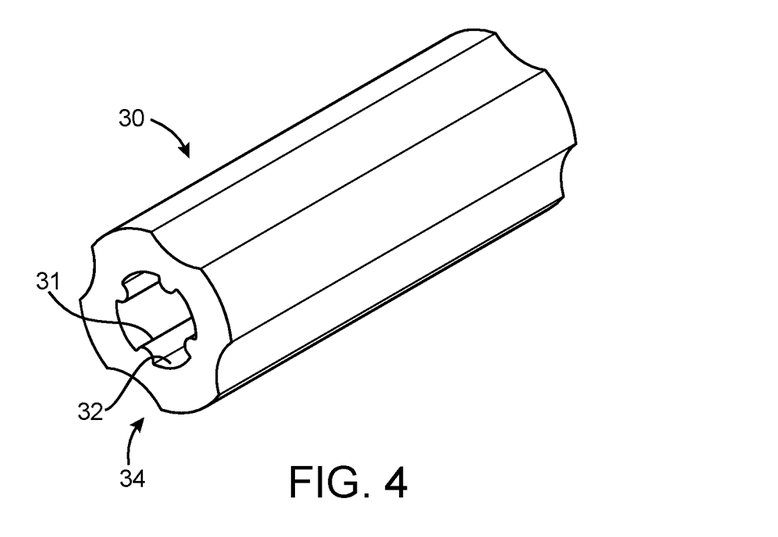
FIG. 4 is a perspective view of the sleeve portion of a body of the collet adapted for being rotated relative to the collar of FIG. 3.

An outer, generally cylindrical body 70 can be rotated relative to collar 20 when the collet 10 is rotationally positioned to form the helix. Body 70 may be formed generally as a one-piece structure or two piece structure. The illustrated embodiment shows body 70 as including an inner sleeve 30 attached within a circular opening of an outer housing 40, which is an example of a two-piece structure for body 70. Perspective views of collar 20 and sleeve 30 are shown in FIGS. 3 and 4. As can be appreciate from FIGS. 2A and 2B, the housing 40 and sleeve 30 of body 70, and the collar 20 each have complimentary openings or passages— sleeve 30 is secured within an opening in housing 40, collar 20 is received within an opening 34 in sleeve 30 and collar 20 has a passage 24 for rod 5.

A geared, or detent-like engagement 22/32 between the collar 20 outer surface 22 and mating inner surface 32 of sleeve 30 may be adopted. A gear-like outer surface 22 having a plurality of teeth 21 is formed on the collar 20, which mates with the surface of opening 32 of sleeve 30, which has complimentary teeth or detents 31, e.g., spaced 90 degrees apart. The sleeve 30 may include scallops 34 opposite each tooth 31 to locally reduce radial stiffness near a tooth 31 so that the tooth 31 will deflect outwardly when the body 70 is rotated relative to the collar 20 to cause a tooth 31 to bear against an adjacent tooth 21 on the collar 20. A close-up illustration of the interaction between the sleeve 30 and collar 20 from FIG. 2A is illustrated in FIG. 2C. Thus, as body 70 is rotated clockwise by an incremental angle, e.g., 10, 15, 20, or 30 degrees depending on the number of teeth on collar 20, tooth 31b deflects outwardly as it bears against tooth 21c. Tooth 31b then begins to deflect radially outward until it clears the apex of tooth 21c, then it snaps back into the valley formed by teeth 21c and 21a.

A passage 41 for rod 1 is provided in housing 40. Thus, as the body 70 is rotated as just described, the rod 1 is rotated about the axis A relative to the collar 20 and the collet 11 to shape the helix, where it is understood there is no relative rotation between rod 5 and neither of collet 11 and collar 20.

As mentioned above, the body 70 need not be formed using the two pieces 30, 40. Alternatively, the body 70 may be formed in one piece, where an opening for receiving the collar 20 within has formed on it teeth 31 for mating with the teeth 21 of the gear-like outer surface 22 of collar 20. In the illustrated embodiment two pieces are shown to illustrate an embodiment where the outer member 40 is made of a relatively stiff material, i.e., metal or hard polymer, while the sleeve 30 is made of a different material for purposes of providing deflectable detents along its inner surface for engagement with the mating teeth 21 of the collar 20.

The collar 20 may be held in place during body 70 rotation relative to collar 20 (to form helix) by a pair of leafs 28a, 28b extending from one side of the collar 20 (e.g., using either one's fingers or a clamp to hold leafs 28a, 28b firmly against the rod 5 while body 70 is rotated about collar 20). Or, when there is a sufficient frictional fit between the rod 5 and inner surface of the collar 20, no additional rotational restraint of collar 20 may be necessary to hold collar 20 in place while body 70 is rotated about axis A to shape rod 1 into a helix.

The collet 10 may include a rotational lock that both prevents the body 70 from rotating relative to the collar 20 and the collet 10 from rotating relative to the rod 5. Such a rotation lock may be necessary to prevent torsional energy in the helix from causing the body 70 to back-drive, thereby unwinding the helix (e.g., if the helix is formed by rotating body 70 clockwise about collar 20, then the rod 1 will apply a reactive counterclockwise torque on the body 70 causing the helix to unravel; that is, rotate counterclockwise, unless body 70 is held in rotation relative to collar 20 and rod 5.

Referring to FIG. 2B, a rotation lock can be provided in the form of a threaded fastener 50 having a threaded portion 50a on its shank. The fastener 50 is received within a circular thru-hole of the body 70 which provides passage of the tip of the fastener 50 into an opening 28c of the collar 20 so that the tip of the fastener 50 can be screwed firmly against the rod 5. The thru-hole 44 includes a mating threading 44a to engage the threads 50a of the fastener 50. When the tip of the fastener 50 is pressed against the rod 5 in the passage 24, the collet 10 may be prevented from rotating about the axis A (i.e., the axis collinear with rod 5 longitudinal axis, see FIG. 1C) relative to the rod 5, and the body 70 also will not rotate relative to the collar 20.

In alternative embodiments no fastener 50 is used. Instead, a tight fit between the rod 5 and collar 20 can hold the collet 10 in place by friction. In another embodiment, the rod 5 may have a threading and the inner surface of collar 20 forms a mating threading. In this embodiment the collet 10 is rotated about the rod 5 to adjust its position relative to the collet 11. Once the desired position for collet 10 is found, the rod 5 is passed through the hole 41 provided in member 40 and the body 70 rotated while the collar 20 is held in place. The threaded engagement between rod 5 and collar 20 can be made sufficiently tight to hold the collar 20 in rotation while the body 70 is rotated to form the rod 1 into a helix. Once the helix-shaped rod 1 is formed, the rotational position of the body 70 relative to the collar 20 may be maintained by the interlocking teeth 21/31 between the sleeve 30 and collar 20. A close-up of the interlocking teeth is shown in FIG. 2C.

When configuring the assembly of FIG. 1A for a particular diameter and length tubular medical device, the following steps may be used. First, the rods 1 and 5 are attached to collet 11. Next, the stent is placed over the rods 1, 5. The other ends of the rods are then passed through their respective through-holes 41 and 24 in collet 10. The amount of rod 1 between collets 10 and 11 may depend on the type of helix formed, length and diameter of the medical device. The rod 5 position is dependent on the amount of space desired between the medical device, if any, and the faces of the collets. Once this position is determined, the collar 20 is then fixed in rotation relative to the rod 5, e.g., by gripping leafs 28a, 28b manually, or using a clamp, to prevent collar 20 from rotating relative to the rod 5. Alternatively, there may be sufficient frictional contact between the wall of passage 24 and outer surface of rod 5 so that leafs 28a, 28b are not necessary. The body 70 is then rotated or clocked about the collar 20 to form the desired helix shape. During the process of forming the helix-shaped rod 1 the amount of rod 1 between the collets may need adjustment to achieve the desired diameter and/or revolutions in the helix extending between the collets. This may be done by gripping end 1a of rod 1 (to the right of collet 10 in FIG. 1A) pushing it to the left or pulling to the right, explained in greater detail, below, in connection with FIGS. 5-8. Once the helix-shaped rod 1 is formed, the engaging teeth 21/31 between the collar 20 and sleeve 30 can hold the helix shape, i.e., prevent the body 70 from rotating relative to the collar, thereby undoing the helix. Or a rotation lock, e.g., fastener 50, may be used to fix the collar 20, rod 5 and body 70 in rotation. This method is illustrated in FIG. 9.

Referring again to FIG. 1A, in another embodiment the assembly may include the first collet 11 and an alternative to the second collet where there is no sleeve 30 or collar 20 used (housing 40'). Rather, the collet includes the housing having a central passage for the rod 5 and hole 41 for rod 1. In this embodiment the rod 1 may be shaped to circumscribe the rod 5 (to provide the supporting surface for the stent) by rotating the second collet housing 40' about the rod 5 which is fixed to the collet 10. Once the desired rod 1 shape is made, the fastener 50 may be pressed into the rod 1 (as before) to hold the collet 40' in place relative to the collet 10, thereby maintain the shape of the rod 1. This method is also illustrated in FIG. 9.

Alternatively, the fastener 50 may be located on the collet 10 to fix the rod 5 to the collet 11 after the rod 1 is shaped by rotation of collet 10 and rod 1 (rod 1 is fixed to collet 10). In this embodiment, therefore, the assembly would proceed as follows. First, the stent is placed on the rod 5, which is attached to collet 10. The rod 5 end is then inserted into the collet 11. The rod 1 is also attached to the collet 10 and 11. After the collet 10 and rod 5 are rotated relative to the collet 11 to form the desired shape of rod 1, the fastener is used to fix the collet 11 in rotation about axis A to the rod 5.

As will be understood, rod 1 needs to have inherent flexural rigidity, i.e., bending stiffness, as well as relatively large elastic range to enable to be shaped into various helical forms when a torque is applied, i.e., when body 70 is rotated relative to collet 11 in FIG. 1A. It has been found that a super-elastic material, such as Nitinol, can perform this function adequately.

FIGS. 5-8 show a range of helical shapes for supporting differently-sized tubular medical devices according to the disclosure. The same length rod 1 is used in each of FIGS. 5-8. As shown, different amounts of rod 1 are to the right of collet 10 (note different lengths for end 1a among the illustrations) to create larger/smaller diameters and/or more/less revolutions of the helix, depending on the type of tubular medical device. Some medical devices require more support, thus more revolutions are formed, while others require less, thus less revolutions are formed.

To accommodate a larger diameter stent, for example, or where more revolutions of the helix are desired to provide greater support for a stent, more rod 1 material is disposed between the collets before body 70 is rotated about collar 20. When fewer revolutions or turns, or a smaller diameter of the helix is desired then less of the rod 1 material is between the collets before body 70 is rotated about collar 20. The amount of rod 1 material between the collets may be adjusted as the body 70 is rotated to make adjustments. The distance between the collets may also be adjusted while the helix is being formed to arrive at the desired shape. This can be done by gripping the leafs 28a, 28b to push the collet 10 closer or farther from the collet 11 with one hand, while the body 70 is rotated relative to the collar 20 with the other hand.

When a geared interaction 22/32 between collar 20 and body 70 is provided, the rotational amounts applied may be easily controlled to arrive at the desired size and/or number of revolutions. Alternatively, it may be predetermined how much of rod 1 needs to be between the collets to arrive at the desired shape. That is, one can calculate the length of the rod 1 between the collets needed to arrive at the desired number of revolutions or diameter of the helix. Similarly, the amount of rotations of body 70 may be predetermined or calculated.

Figure 5:
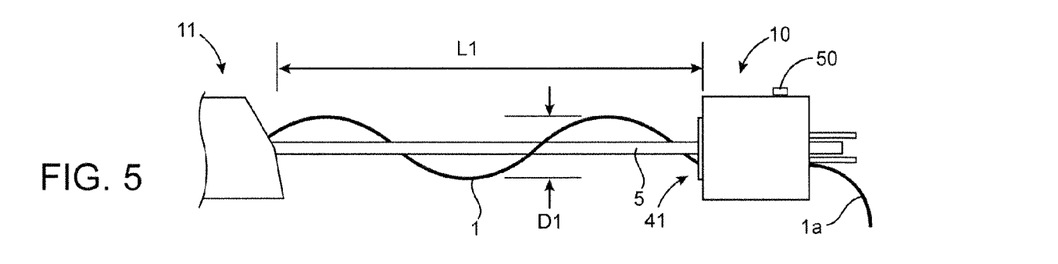
FIG. 5 is a first arrangement of the assembly of FIG. 1A having the rod shaped to provide a support of length L1 and diameter D1 for a medical device. There is about one and one half revolutions of a helix formed in the rod.

FIG. 5 shows a first support for a medical device. The supporting helix has a diameter D1 and the collets 10, 11 are spaced apart by a length L1. If more of rod 1 is pulled through opening 41 in housing and collet 10 moved closer to collet 11, then the same number of revolutions and diameter of the helix may be formed for a shorter stent (L2<L1), as illustrated in FIG. 6.

Figure 7:
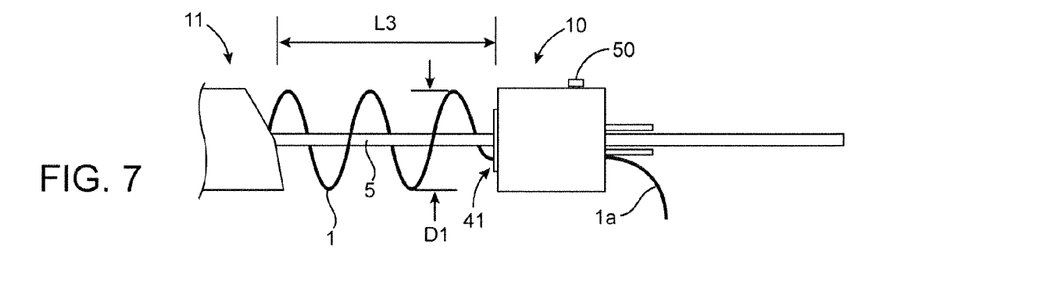
FIG. 7 is a third arrangement of the assembly of FIG. 1A having the rod shaped to provide a support of length L3 and diameter D1 for a medical device. There are about two and one half revolutions of a helix formed in the rod.

In FIG. 7 the assembly is made for a shorter stent but with an increased number of revolutions or turns in the helix. Thus, more of rod 1 may be needed between the collets to create more revolutions, even though L3 is less than L2.

Figure 6:
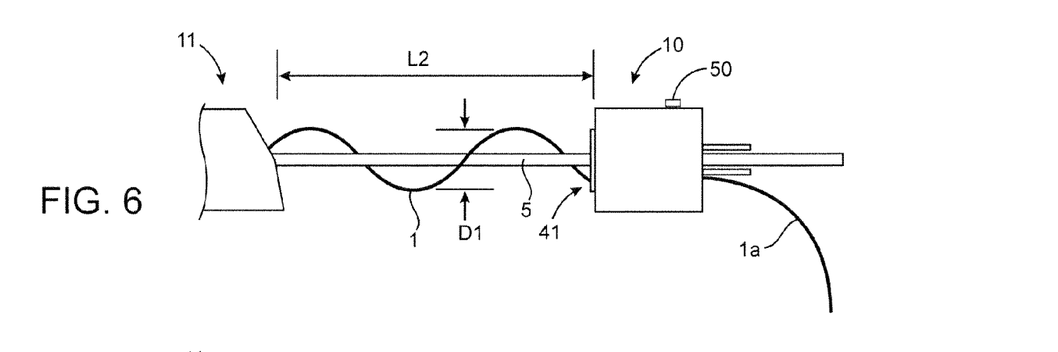
FIG. 6 is a second arrangement of the assembly of FIG. 1A having the rod shaped to provide a support of length L2 and diameter D1 for a medical device.
Figure 8:
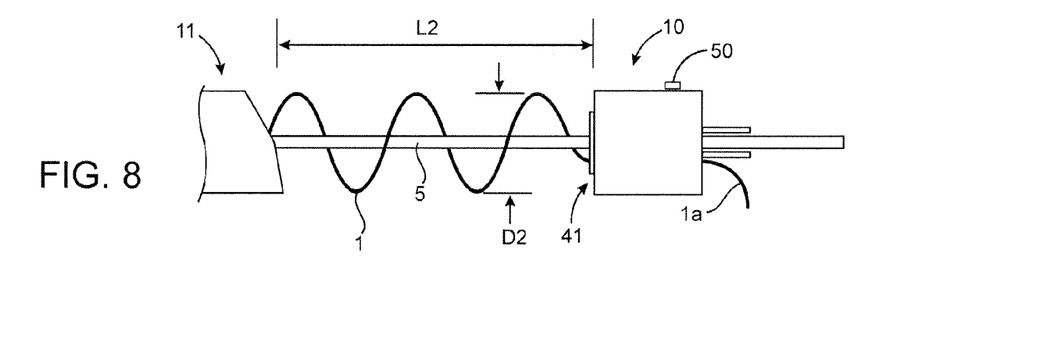
FIG. 8 is a fourth arrangement of the assembly of FIG. 1A having the rod shaped to provide a support of length L2 and diameter D2 for a medical device. Diameter D2 is greater than diameter D1.
Figure 9:
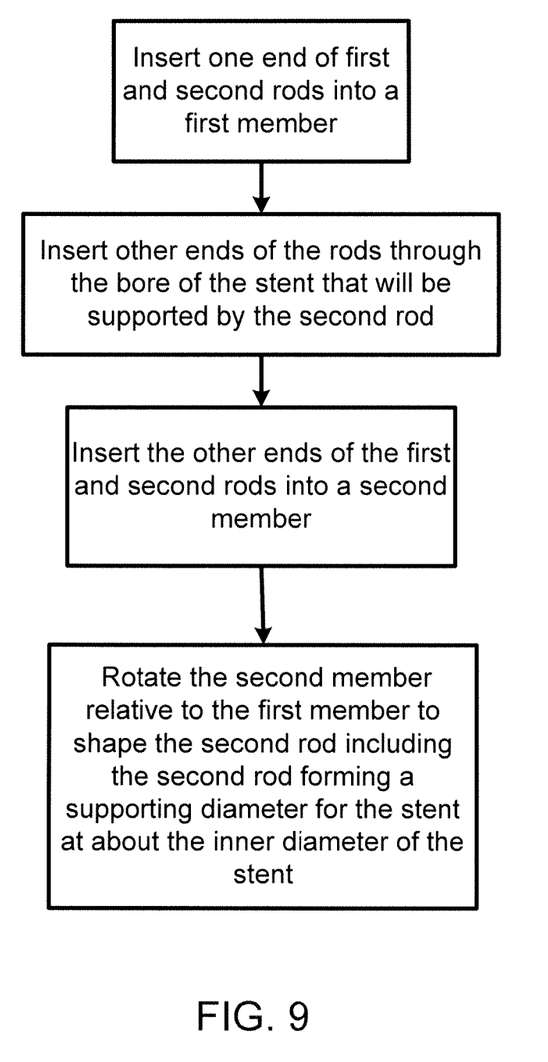
FIG. 9 is a flowchart showing steps for assembling a stent support device according to another aspect of the invention.

FIG. 8 shows an assembly for a stent that has both a larger diameter and more revolutions than the assembly of FIG. 6. IN this case, more rod 1 material is needed between the collets than in the case of FIG. 6.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in claims should not be construed to limit the invention to the specific embodiments disclosed in the specification. Rather, the scope of the invention is to be determined entirely by claims, which are to be construed in accordance with established doctrines of claim interpretation.

The invention claimed is:

1. A method of making a support for a tubular medical device, comprising:
    disposing the medical device on a rod extending between first and second members; and
    while the medical device is disposed on the rod, rotating the second member relative to the first member to cause the rod to rotate about a rotation axis, whereupon the rod is shaped into a full or partial helix supporting the medical device.

2. The method of claim 1, further including the step of changing a length of a portion of the rod that extends from the first member to the second member.

3. The method of claim 2, wherein the length is decreased to decrease a diameter of the full or partial helix, or increased to increase the diameter of the full or partial helix.

4. The method of claim 2, wherein the length is decreased to decrease a number of full revolutions, or the degree of a partial revolution in the full or partial helix, or increased to increase the number of full revolutions, or the degree of a partial revolution in the full or partial helix.

5. The method of claim 2, wherein the rod passes through a passage in the second member, and the length is changed by moving the rod through the passage.

6. The method of claim 5, wherein the second member has an axis for the rotation of the second member relative to the first member and the passage is offset from the axis.

7. The method of claim 1, further including locking the second member in rotation relative to the first member after the rod is shaped into the full or partial helix.

8. The method of claim 7, further including using a second rod extending from the first member to the second member, wherein the second member is locked in rotation by a fastener engaged with both the second member and the second rod.

9. The method of claim 7, wherein the second member is locked in rotation by a detent mechanism.

10. A method, comprising:
    using a rod disposed within a bore of a tubular medical device, wherein a proximal end of the rod is attached to a first member and a distal end of the rod is attached to a second member; and
    supporting the medical device on the rod by rotating the second member relative to the first member, wherein the rotation of the second member relative to the first member shapes the rod into a full or partial helix.

11. The method of claim 10, further including using a second rod, at least a portion of which extends between the first and second members, wherein the supporting step includes moving the second member over the second rod so as to move the second member closer or farther away from the first member to support the medical device.

12. The method of claim 10, wherein the supporting step includes increasing a diameter of the rod by displacing the second member towards the first member.

13. The method of claim 10, wherein the supporting step increases a degree of the partial, or number of the full revolutions of the helix.

14. The method of claim 10, wherein the second member is locked by a frictional engagement, a fastener or a detent mechanism with a second rod attached to the first member.

15. The method of claim 10, wherein the rod is a first rod, and wherein the first rod at least partially circumscribes a longitudinal axis of a second rod attached to the first member.

16. The method of claim 10, wherein the first and second members are collets and the medical device is disposed between the collets.

17. A method, comprising:
    using a medical device disposed on a rod attached to first and second members, wherein at least a portion of the rod extends between the first and second members; and
    supporting the medical device by the rod portion, including the steps of increasing or decreasing a length of the rod portion and shaping the rod portion as a full or partial helix;
    wherein the rod has a proximal end attached to the first member, a medial portion between the first and second members and supporting the medical device, and a distal portion not between the first and second members and not supporting the medical device.

18. The method of claim 17, wherein the supporting step includes increasing a diameter of the full or partial helix by increasing a length of the medial portion, whereupon a length of the distal portion decreases.

19. The method of claim 17, wherein the supporting step includes increasing a degree of the partial, or a number of revolutions of the full helix by increasing a length of the medial portion, whereupon a length of the distal portion decreases.

20. The method of claim 17, wherein the medical device is between the first and second members.

21. The method of claim 17, wherein the rod passes through a passage provided in the second member.

\* \* \* \* \*